(12) United States Patent
Monteux et al.

(10) Patent No.: US 11,401,390 B2
(45) Date of Patent: Aug. 2, 2022

(54) POLYMER MEMBRANE AND METHODS OF MANUFACTURING THEREOF

(71) Applicants: Centre national de la recherche scientifique, Paris (FR); ECOLE SUPERIEURE DE PHYSIQUE ET DE CHIMIE INDUSTRIELLES DE LA VILLE DE PARIS, Paris (FR); Sorbonne Université, Paris (FR)

(72) Inventors: Cécile Monteux, Paris (FR); Julien Dupré De Baubigny, Ivry sur Seine (FR); Mathilde Reyssat, Antony (FR); Patrick Perrin, Paris (FR); Nadège Pantoustier, Brunoy (FR)

(73) Assignees: CENTRE NATIONAL DE LA RECHERCHE SCIENTIFIQUE, Paris (FR); ECOLE SUPERIEURE DE PHYSIQUE ET DE CHIMIE INDUSTRIELLES DE LA VILLE, Paris (FR); SORBONNE UNIVERSITÉ, Paris (FR)

( * ) Notice: Subject to any disclaimer, the term of this patent is extended or adjusted under 35 U.S.C. 154(b) by 423 days.

(21) Appl. No.: 16/494,620

(22) PCT Filed: Mar. 16, 2018

(86) PCT No.: PCT/EP2018/056737
§ 371 (c)(1),
(2) Date: Sep. 16, 2019

(87) PCT Pub. No.: WO2018/167297
PCT Pub. Date: Sep. 20, 2018

(65) Prior Publication Data
US 2020/0131320 A1 Apr. 30, 2020

(30) Foreign Application Priority Data
Mar. 17, 2017 (EP) .................................. 17161648

(51) Int. Cl.
*C08J 5/18* (2006.01)
*B01J 13/16* (2006.01)
(Continued)

(52) U.S. Cl.
CPC ................. *C08J 5/18* (2013.01); *B01J 13/16* (2013.01); *C08L 33/02* (2013.01); *C08L 71/02* (2013.01);
(Continued)

(58) Field of Classification Search
None
See application file for complete search history.

(56) References Cited

U.S. PATENT DOCUMENTS

2009/0053160 A1 2/2009 Khoshdel et al.
2015/0284665 A1* 10/2015 Bone ..................... A61Q 5/12
424/401
(Continued)

FOREIGN PATENT DOCUMENTS

EP 1462157 9/2004
KR 20040084364 10/2004

OTHER PUBLICATIONS

International Search Report for PCT/EP2018/056737, dated Apr. 26, 2018.
(Continued)

*Primary Examiner* — Jeffrey D Washville
(74) *Attorney, Agent, or Firm* — B. Aaron Schulman, Esq.; Stites & Harbison, PLLC

(57) ABSTRACT

This invention relates to a polymer membrane comprising a hydrogen bond donor polymer and a hydrogen bond acceptor polymer and to the use of such membrane as the shell of a capsule. The invention also relates to a method of manufacturing a polymer membrane comprising a step of contacting an aqueous phase comprising a first polymer, and an (Continued)

oil phase comprising a second different polymer; wherein one polymer is a hydrogen bond donor polymer and the other polymer is a hydrogen bond acceptor polymer. The invention also relates to a method of encapsulation comprising a step of manufacturing a polymer membrane.

19 Claims, 2 Drawing Sheets

(51) Int. Cl.
*C08L 33/02* (2006.01)
*C08L 71/02* (2006.01)

(52) U.S. Cl.
CPC ........ *C08J 2333/02* (2013.01); *C08J 2371/02* (2013.01); *C08J 2433/02* (2013.01); *C08J 2471/02* (2013.01); *C08L 2207/53* (2013.01)

(56) References Cited

U.S. PATENT DOCUMENTS

2019/0016859 A1* 1/2019 Kornfield .............. C08L 101/02
2019/0031981 A1   1/2019 Givaudan et al.

OTHER PUBLICATIONS

Written Opinion of the International Searching Authority for PCT/EP2018/056737, dated Apr. 26, 2018.

* cited by examiner

POLYMER MEMBRANE AND METHODS OF MANUFACTURING THEREOF

FIELD OF INVENTION

The present invention pertains to the field of polymer membranes and to the field of encapsulation. The present invention is especially related to polymer membranes for use in methods of encapsulation.

BACKGROUND OF INVENTION

Encapsulation of substances of interest is widely used to store, protect or administrate the substance of interest, especially in pharmaceutical and medicinal fields, but also for cosmetics, perfumes, foods and many others household products. The capsules are generally spherical or pseudo-spherical and comprise a core of a substance of interest which is completely surrounded by a shell membrane being generally polymeric material.

Typical method of encapsulation involves dispersing the substance of interest in a solution comprising a precursor of a polymeric material and forming the shell around droplets of the substance of interest by chemical reaction e.g. by polymerization or by crosslinking. However, these methods can lead to the presence of reaction residues such as monomers and/or degradation products of chemically reactive polymers, thus rendering the capsules unsuitable for many uses or requiring complicated and costly cleaning post-treatments.

Alternative encapsulation methods are based on the formation of the shell by means of complexation of at least two oppositely charged polymers. By contacting a polycation together with a polyanion, a polymeric complex can be formed, the properties of the complex depending of the nature of the charged groups within the polymer. However, these methods require the shell-forming polymers to have ionizable functions and to be placed in conditions wherein the polymers are effectively charged with opposite charges which are usually limited to a narrow range of conditions. Moreover, high amounts of additional agents such as acids, base or surfactants are generally required in order to obtain the charged polymers. Moreover, charged polymers remaining in the final shell membrane might cause safety issues, especially polycations which are known to be irritating.

Encapsulation methods of the art often lead to capsules wherein the shell consists in a very thin membrane. Moreover, the shell obtained by the methods of the art typically exhibit low rigidity, characterized by an interfacial shear storage modulus G' measured at 1 rad/s lower than 0.2 N/m (Pa·m) or lower than 0.1 N/m (Pa·m). Although some uses can exploit such properties, they might be disadvantageous for others applications, especially if the capsules are exposed to aggressive transport and/or storage conditions or when delayed release of the substance of interest is desired.

Therefore, there is a need for shell membranes exhibiting improved thickness and physical resistance. There also is a need for simpler, less expensive and more eco-friendly methods of manufacturing membranes, especially for encapsulation purposes, and for encapsulation methods leading to capsules having a thick and solid membrane.

The Applicant surprisingly found that a bi-polymer membrane of high thickness and resistance can be efficiently manufactured by means of contacting a hydrogen bond donor polymer and a hydrogen bond acceptor polymer bearing appropriate chemical functions, each polymer being in a different phase of a biphasic system. Advantageously, the method of the invention allows the manufacture of a polymer shell membrane by a one-step process, without the need of high amounts (if any) of additional agents in the reactional medium and without having to clean and/or post-treat of the shell. The method of the invention for manufacturing the polymer membrane is easy to perform, and does not require any specific equipment.

The polymer membrane of the invention can be used as such, or involved in an encapsulation process to obtain capsules including an oil phase or an aqueous phase surrounded by a thick and solid protective shell.

SUMMARY

This invention relates to a polymer membrane comprising a hydrogen bond donor polymer and a hydrogen bond acceptor polymer;
   wherein the hydrogen bond donor polymer is made of one or more monomers, and comprises:
      a hydrogen bond donor group being carboxyl, wherein from 50% to 100%, preferably from 75% to 100%, in number of the monomer units relative to the total number of monomer units in the polymer comprise such a hydrogen bond donor group; and
      a lateral substituent comprising at least one hydrophobic group selected from alkyl, cycloalkyl and aryl, wherein from 50% to 100%, preferably from 75% to 100%, in number of the monomer units relative to the total number of monomer units in the polymer comprise such a lateral substituent;
   wherein the hydrogen bond acceptor polymer is made of one or more monomers, and comprises:
      a hydrogen bond acceptor group being ether, wherein from 50% to 100%, preferably from 75% to 100%, in number of the monomer units relative to the total number of monomer units in the polymer comprise such a hydrogen bond acceptor group; and
      a lateral substituent comprising at least one hydrophobic group selected from alkyl, cycloalkyl and aryl, wherein from 50% to 100%, preferably from 75% to 100%, in number of the monomer units relative to the total number of monomer units in the polymer comprise such a lateral substituent; and
   wherein the shear storage modulus G' of the polymer membrane, measured at 1 rad/s, is at least 0.5 N/m, preferably at least 1.0 N/m, more preferably at least 5.0 N/m.

According to an embodiment, the hydrogen bond donor group or the hydrogen bond acceptor group; and the lateral substituent comprising the hydrophobic group are present on the same monomer, in the hydrogen bond donor polymer and/or in the hydrogen bond acceptor polymer respectively.

According to an embodiment, the hydrogen bond donor polymer is poly(methacrylic) acid.

According to an embodiment, the hydrogen bond acceptor polymer is selected from polypropylene oxide and poloxamers, wherein the poloxamer comprises an amount of polypropylene oxide monomer ranging from 50% to 100%, preferably from 75% to 100%, in number of monomers relative to the total number of monomer units in the poloxamer.

According to an embodiment, the polymer membrane does not comprise any charged polymer.

This invention also relates to a method of manufacturing a polymer membrane comprising a step of contacting: an aqueous phase comprising a first polymer, and an oil phase comprising a second different polymer;

wherein one of the first and second polymers is a hydrogen bond donor polymer and the other is a hydrogen bond acceptor polymer;

wherein the hydrogen bond donor polymer is made of one or more monomers, and comprises:
  a hydrogen bond donor group selected from carboxyl and hydroxyl, wherein from 50% to 100%, preferably from 75% to 100%, in number of the monomer units relative to the total number of monomer units in the polymer comprise such a hydrogen bond donor group; and
  a lateral substituent comprising at least one hydrophobic group selected from alkyl, cycloalkyl, aryl, heteroaryl, secondary and tertiary amine, secondary and tertiary amide, and ester, wherein from 50% to 100%, preferably from 75% to 100%, in number of the monomer units relative to the total number of monomer units in the polymer comprise such a lateral substituent; and wherein the hydrogen bond acceptor polymer is made of one or more monomers, and comprises:
  a hydrogen bond acceptor group selected from ether, ester, ketone and amide, wherein from 50% to 100%, preferably from 75% to 100%, in number of the monomer units relative to the total number of monomer units in the polymer comprise such a hydrogen bond acceptor group; and
  a lateral substituent comprising at least one hydrophobic group selected from alkyl, cycloalkyl, aryl, heteroaryl, secondary and tertiary amine, secondary and tertiary amide, and ester, wherein from 50% to 100%, preferably from 75% to 100%, in number of the monomer units relative to the total number of monomer units in the polymer comprises such a lateral substituent; and wherein at least one among the first and second polymers is not a charged polymer.

According to an embodiment, the hydrogen bond donor group or the hydrogen bond acceptor group; and the lateral substituent comprising the hydrophobic group are present on the same monomer, in the hydrogen bond donor polymer and/or in the hydrogen bond acceptor polymer respectively.

According to an embodiment, the hydrogen bond donor polymer is poly(methacrylic) acid.

According to an embodiment, the hydrogen bond acceptor polymer is selected from polypropylene oxide and poloxamers, wherein the poloxamer comprises an amount of polypropylene oxide monomer ranging from 50% to 100%, preferably from 75% to 100%, in number of monomers relative to the total number of monomer units in the poloxamer.

According to an embodiment, both first and second polymers are not charged polymers.

According to an embodiment, the shear storage modulus of the polymer membrane manufactured by the method, measured at 1 rad/s, is at least 0.5 N/m, preferably at least 1.0 N/m, more preferably at least 5.0 N/m.

This invention also relates to a capsule comprising a core and a shell around said core, wherein the shell comprises a polymer membrane according to the invention.

This invention also relates to a composition comprising a polymer membrane polymer membrane according to the invention and/or comprising capsules according to the invention.

This invention also relates a to method of encapsulation comprising: a step of forming around a core a polymer membrane according to the invention; and/or a step of forming around a core a polymer membrane to manufacture a capsule according to the invention.

This invention also relates to a method of encapsulation comprising the method of manufacturing a polymer membrane according to the invention.

DEFINITIONS

In the present invention, the following terms have the following meanings:

"About" preceding a number means plus or less 10% of the value of said figure.

"Alkyl" refers to a linear or branched saturated hydrocarbon chain of general formula —$C_nH_{2n+1}$ wherein n is a number greater than or equal to 1, typically containing 1 to 16 carbon atoms, preferably 1 to 8 carbon atoms, more preferably 1 to 4 carbon atoms. Examples of alkyl groups are methyl, ethyl, n-propyl, isopropyl, butyl and its isomers (e.g. n-butyl, i-butyl and t-butyl), pentyl and its isomers, hexyl and its isomers.

"Cycloalkyl" refers to a cyclic alkyl group as defined above, including monocyclic or bicyclic alkyl groups. Cycloalkyl groups comprise 3 or more carbon atoms in the ring, typically containing 3 to 16 carbon atoms, preferably from 3 to 8 carbon atoms, more preferably from 3 to 6 carbon atoms in the ring. Examples of cycloalkyl groups are cyclopropyl, cyclobutyl, cyclopentyl and cyclohexyl.

"Amine" refers to a group derived from ammoniac ($NH_3$) by substitution of one or more hydrogen atoms with an organic radical. Amine preferably refers to primary amine (—$NH_2$), secondary amine (—NHR) and tertiary amine (—NRR'), wherein R and R' are alkyl, cycloalkyl, aryl, heteroaryl groups, or combinations thereof, preferably alkyl groups. Therefore "Amine" includes monoalkylamine and dialkylamine groups, for example methylamine (—$NHCH_3$) and dimethylamine (—N$(CH_3)_2$). "Amine" also includes cyclic tertiary groups, wherein R and R' form together one unique substituent.

"Amide" refers to —C(O)—NRR' group, wherein R and R' are preferably hydrogen, alkyl, cycloalkyl, aryl, heteroaryl groups, or combinations thereof. Amide preferably refers to primary amide (—$CONH_2$), secondary amide (—CONHR) and tertiary amide (—CONRR'), wherein R and R' are preferably alkyl groups. Therefore "Amide" includes monoalkylamide and dialkylamide groups, for example methylamide (—$CONHCH_3$) and dimethylamide (—$CON(CH_3)_2$). "Amide" also includes cyclic tertiary groups, wherein R and R' form together one unique substituent.

"Aryl" refers to a polyunsaturated, aromatic hydrocarbon chain having a single ring (i.e. phenyl) or multiple rings fused together (e.g. naphtyl) or linked covalently, wherein at least one ring is aromatic, typically containing 5 to 16 carbon atoms, preferably 5 to 10 carbon atoms, more preferably 5 or 6 carbon atoms. "Aryl" also refers to the partially hydrogenated derivatives of the carbocyclic systems enumerated herein. Examples of aryl groups are phenyl, biphenylyl, biphenylenyl, 5- or 6-tetralinyl, naphthalen-1- or-2-yl, 4-, 5-, 6 or 7-indenyl, 1-2-, 3-, 4- or 5-acenaphtylenyl, 3-, 4- or 5-acenaphtenyl, 1- or 2-pentalenyl, 4- or 5-indanyl, 5-, 6-, 7- or 8-tetrahydronaphthyl, 1,2,3,4-tetrahydronaphthyl, 1,4-dihydronaphthyl, 1-, 2-, 3-, 4- or 5-pyrenyl.

"Capsules" refers to an article comprising a core and a shell around said core, typically for use as a dosage form such as soft-shell capsules. The core preferably comprises or consists of a substance of interest and the shell is preferably a polymer membrane.

"Charged monomer" refers to a monomer bearing at least one electric charge, wherein the charge can be positive or negative.

"Charged polymer" refers to a polymer bearing at least 5% of charged monomers. A polymer bearing at least 5% of positively charged monomers is referred as "polycation" and polymer bearing at least 5% of negatively charged monomers is referred as "polyanion". Examples of charged polymers are poly(styrene) sulfonate and polymers comprising quaternized amines.

"Ester" refers to —COOR group, wherein R is preferably alkyl, cycloalkyl, aryl, heteroaryl group, or combinations thereof; preferably alkyl group.

"Ether" refers to —OR group, wherein R is preferably alkyl, cycloalkyl, aryl, heteroaryl group, or combinations thereof; preferably alkyl group.

"From . . . to . . ." or "Ranging from . . . to . . ." including two number are synonyms and defines an interval which includes its boundaries, for example "from 5 to 10" or "ranging from 5 to 10" includes "5" and "10" values and all values within the interval.

"Heteroaryl" refers to an aryl group as defined above, wherein one or more carbon atoms in one or more aromatic rings are replaced by oxygen, nitrogen or sulfur atoms, and wherein the nitrogen and sulfur heteroatoms may optionally be oxidized and the nitrogen heteroatoms may optionally be quaternized. Non-limiting examples of such heteroaryl are pyrrolyl, furanyl, thiophenyl and pyrazolyl.

"Higher than . . ." refers to an interval wherein the lower value delimiting the interval is included therein. For example, "higher than 5" includes "5" and any value strictly higher than 5.

"Hydrogen bond acceptor" refers to a molecule or group comprising a highly electronegative atom such as nitrogen or oxygen atom, the electronegative atom being susceptible to attract by means of electrostatic field a hydrogen atom nearby, thus forming a hydrogen bond with a hydrogen bond donor group. Examples of hydrogen bond acceptor are groups comprising nitrogen or oxygen atoms with non-bonding doublets such as ether, ester, ketone and amide groups, or non-quaternized amine groups.

"Hydrogen bond donor" refers to a molecule or group comprising an atom, or a group of atoms, wherein a hydrogen atom is covalently bound to a highly electronegative atom such as nitrogen, oxygen, or fluorine atom, the hydrogen atom being susceptible to be attracted by the electrostatic field of another highly electronegative atom nearby, thus forming a hydrogen bound with a hydrogen bond acceptor group. Examples of hydrogen bond donor are groups comprising hydroxyl, such as carboxylic acid and alcohol groups.

"Hydrophobic group" refers to a group, typically a non-polar and non-charged group, which reduces the solubility in polar solvents (such as water or ethanol) of a molecule including this hydrophobic group, compared to the same molecule being deprived of this hydrophobic group. Examples of hydrophobic groups are alkyl, cycloalkyl and aryl groups, and groups comprising such groups, for example secondary and tertiary amine or amide.

"Ketone" refers to —C(O)R group, wherein R is preferably alkyl, cycloalkyl, aryl, heteroaryl groups, or combinations thereof; preferably alkyl group.

"Lateral substituent" refers to a group which is comprised in a polymer but which is not included within the main polymeric chain of the polymer. For example, the lateral substituents in poly(methacrylic) acid (PMAA) are methyl and carboxylic acid groups. For example, the lateral substituent in poly(propyl) oxide (PPO) is methyl group, but not the ether moiety, because the oxygens atoms are included the polymeric chain.

"Lower than . . ." refers to an interval wherein the higher value delimiting the interval is included therein. For example, "lower than 5" includes "5" and any value strictly lower than 5.

"Membrane" or "Polymer membrane" refers to a structure being relatively thin compared to its size and consisting essentially of polymers. Membranes are useful in separating two media by preventing a material, or a part of a material, to pass from one to one medium to the other. Preferably, membranes are used to separate a substance of interest from the external environment, e.g. for handling and/or preservation purposes, for example as part of the shell of a capsule.

"Interfacial shear modulus", "Interfacial shear storage moduli" and "Interfacial shear loss moduli" (which are not synonymous) are defined as follows: the interfacial shear modulus, G, in N/m, is determined from interfacial shear rheology measurements consisting in applying a controlled interfacial shear stress and measuring the interfacial shear deformation. The interfacial shear modulus, G is the ratio of the interfacial shear stress divided by the interfacial shear deformation. When an oscillatory shear stress is applied to the interface, the deformation is also oscillatory. The interfacial modulus is a complex number with a real part, G' or $G'_s$, the interfacial shear storage modulus and an imaginary part, G" or $G''_s$ the interfacial shear loss modulus. The absolute value of the interfacial shear modulus is G $[(G')^2+(G'')^2]^{1/2}$.

"PAA" refers to poly(acrylic) acid.
"PEAA" refers to poly(ethylacrylic) acid.
"PEO" refers to polyethylene oxide.
"PDMA" refers to poly(N,N-dimethylacrylamide).
"PMAA" refers to poly(methacrylic) acid.
"PNIPAAM" refers to poly(N-isopropylacrylamide).
"PPO" refers to polypropylene oxide.
"PSMA" refers to styrene-maleic acid copolymer.
"PVA" refers to poly(vinyl) alcohol.
"PVAc" refers to poly(vinyl) acetate.
"PVCL" refers to poly(N-vinyl caprolactame).
"PVP" refers to poly(vinylpyrrolidone).

DETAILED DESCRIPTION

This invention relates to a polymer membrane comprising a hydrogen bond donor polymer and a hydrogen bond acceptor polymer.

Said polymer membrane is obtained by the formation of hydrogen bonds between the hydrogen bond donor polymer and the hydrogen bond acceptor polymer. Specifically, the polymer membrane according to the invention does not involve any covalent bond and/or crosslink between the hydrogen bond donor polymer and the hydrogen bond acceptor polymer.

According to an embodiment, the invention relates to a polymer membrane comprising one hydrogen bond donor polymer and one hydrogen bond acceptor polymer.

According to an embodiment, the hydrogen bond donor polymer is made of one or more monomers, and comprises hydrogen bond donor groups and lateral substituents comprising at least one hydrophobic group.

In one embodiment, from 25 to 100%, preferably from 50% to 100%, more preferably from 75% to 100%, even more preferably from 90 to 100%, in number of the monomer units relative to the total number of monomer units in the hydrogen bond donor polymer comprise such hydrogen bond donor groups. In one specific embodiment, the polymer comprises only monomers bearing such hydrogen bond donor groups.

In one embodiment, from 25 to 100%, preferably from 50% to 100%, more preferably from 75% to 100%, even more preferably from 90 to 100%, in number of the monomer units relative to the total number of monomer units in the hydrogen bond donor polymer comprise such lateral substituents. In one specific embodiment, the polymer comprises only monomers bearing such lateral substituents.

In one embodiment, the hydrogen bond donor polymer comprises:
  hydrogen bond donor groups selected from carboxyl (—COOH) and hydroxyl (—OH); and
  lateral substituents comprising at least one hydrophobic group selected from alkyl, cycloalkyl, aryl, heteroaryl, secondary and tertiary amine, secondary and tertiary amide, and ester.

In one specific embodiment, the hydrogen bond donor group is carboxyl (—COOH). In one specific embodiment, the hydrophobic group is selected from alkyl, cycloalkyl and aryl such as methyl, ethyl, propyl, butyl, phenyl or benzyl. In one further specific embodiment, the hydrophobic group is methyl. In one specific embodiment, the hydrophobic group comprises from 1 to 12, preferably from 1 to 6, more preferably from 1 to 3 carbon atoms.

In one embodiment, the hydrogen bond donor group and the lateral substituent comprising at least one hydrophobic group are present on the same monomer in the hydrogen bond donor polymer.

In one embodiment, the hydrogen bond donor polymer is selected from acrylic polymers such as poly(methacrylic) acid (PMAA); co-polymers of polymeric alcohols and polymeric esters such as polyvinyl alcohol (PVA)-polyvinyl acetate (PVAc) copolymers; polysaccharides comprising hydrophobic groups; and derivatives thereof; and copolymers thereof.

In one specific embodiment, the hydrogen bond donor polymer is selected from poly(methacrylic) acid (PMAA), poly(ethylacrylic) acid (PEAA), styrene-maleic acid copolymer (PSMA), and derivatives thereof, and copolymers thereof. In one more specific embodiment, the polymer is selected from poly(methacrylic) acid (PMAA), poly(ethylacrylic) acid (PEAA), and copolymers thereof; preferably poly(methacrylic) acid (PMAA).

In one specific embodiment, the hydrogen bond donor polymer is selected from polyvinyl alcohol (PVA)-polyvinyl acetate (PVAc) copolymers. In one more specific embodiment, the polyvinyl alcohol (PVA)-polyvinyl acetate (PVAc) copolymer comprises from 50% to 100%, preferably from 75% to 100%, of polyvinyl alcohol (PVA) monomer, in number of polyvinyl alcohol (PVA) monomer relative to the total number of monomer units in the copolymer.

In one embodiment, the hydrogen bond donor polymer is not poly(acrylic) acid (PAA), i.e. the polymer does not consist of acrylic monomers. In one specific embodiment, the polymer does not comprise any acrylic acid monomer.

According to an embodiment, the hydrogen bond acceptor polymer is made of one or more monomers and comprises hydrogen bond acceptor groups and lateral substituents comprising at least one hydrophobic group.

In one embodiment, from 25 to 100%, preferably from 50% to 100%, more preferably from 75% to 100%, even more preferably from 90 to 100%, in number of the monomer units relative to the total number of monomer units in the hydrogen bond acceptor polymer comprises such hydrogen bond acceptor groups. In one specific embodiment, the polymer comprises only monomers bearing such hydrogen bond acceptor groups.

In one embodiment, from 25 to 100%, preferably from 50% to 100%, more preferably from 75% to 100%, even more preferably from 90 to 100%, in number of the monomer units relative to the total number of monomer units in the hydrogen bond acceptor polymer comprise such lateral substituents. In one specific embodiment, the polymer comprises only monomers bearing such lateral substituents.

In one embodiment, the hydrogen bond acceptor polymer comprises:
  hydrogen bond acceptor groups selected from ether (—OR), ester (—COOR), ketone (—C(O)R) and amide (—C(O)—N—); and
  lateral substituents comprising at least one hydrophobic group selected from alkyl, cycloalkyl, aryl, heteroaryl, secondary and tertiary amine, secondary and tertiary amide, and ester.

In one specific embodiment, the hydrogen bond acceptor group is ether (—O—). In one specific embodiment, the hydrophobic group is selected from alkyl, cycloalkyl and aryl. In one more specific embodiment, the hydrophobic group is selected from alkyl, cycloalkyl and aryl groups comprising from 1 to 12, preferably from 1 to 6, more preferably from 1 to 3 carbon atoms, such as methyl, ethyl, propyl, butyl, phenyl or benzyl. In one further specific embodiment, the hydrophobic group is methyl.

In one embodiment, the hydrogen bond acceptor group and the lateral substituent comprising at least one hydrophobic group are present on the same monomer in the hydrogen bond acceptor polymer.

In one embodiment, the hydrogen bond acceptor polymer is selected from polymers containing ether groups such as polypropylene oxide (PPO), polyethylene oxide (PEO) or poloxamers; co-polymers of polymeric esters and polymeric alcohols such as polyvinyl acetate (PVAc)-polyvinyl alcohol (PVA) copolymers; polymers containing lactame groups like poly(N-vinyl caprolactame) (PVCL), acrylamide polymers such as poly(N-isopropylacrylamide) (PNIPAAM) and poly (N,N-dimethylacrylamide) (PDMA); amino polymers such as poly(dimethylaminoethyl methacrylate) (PDMAEMA); and derivatives thereof; and copolymers thereof.

In one specific embodiment, the hydrogen bond acceptor polymer is selected from polypropylene oxide (PPO) and poloxamers, which are polypropylene oxide (PPO)-polyethylene oxide (PEO) copolymers. In one more specific embodiment, the poloxamer comprises from 25% to 100%, preferably 50% to 100%, more preferably from 75% to 100%, even more preferably from 90 to 100%, of polypropylene oxide (PPO) monomers, in number of polypropylene oxide (PPO) monomer relative to the total number of monomer units in the poloxamer. In one even more specific embodiment, the poloxamer is Pluronic L61, L81, L101, L121, 17R4, 31R4 or L44, L64, P84, P104, P65, P75, P85, P105; preferably Pluronic L121.

In one specific embodiment, the hydrogen bond acceptor polymer is selected from polyvinyl acetate (PVAc)-polyvinyl alcohol (PVA) copolymers. In one more specific embodiment, the polyvinyl acetate (PVAc)-polyvinyl alcohol (PVA) copolymer comprises from 50% to 100%, preferably from 75% to 100%, of polyvinyl acetate (PVAc) monomers, in number of polyvinyl acetate (PVAc) monomer relative to the total number of monomer units in the copolymer.

In one embodiment, the hydrogen bond acceptor polymer is not poly(vinylpyrrolidone) (PVP), i.e. the polymer does not consist of vinylpyrrolidone monomers. In one specific embodiment, the polymer does not comprise any vinylpyrrolidone monomer.

According to an embodiment, the hydrogen bond acceptor polymer and/or the hydrogen bond acceptor polymer has a molecular weight ranging from 100 to 10 000 000 g/mol, preferably from 1 000 to 1 000 000 g/mol. According to an embodiment, the hydrogen bond donor polymer has a molecular weight ranging from 10 000 to 1 000 000 g/mol, preferably from 50 000 to 200 000 g/mol. According to an embodiment, the hydrogen bond acceptor polymer has a molecular weight ranging from 1 000 to 100 000 g/mol, preferably from 2 000 to 8 000 g/mol.

According to an embodiment, the polymeric chain of the hydrogen bond acceptor polymer and/or of the hydrogen bond acceptor polymer do not comprise any metal or metalloid atoms in their polymeric chain. In one embodiment, the polymeric chain of the hydrogen bond acceptor polymer and/or of the hydrogen bond acceptor polymer comprises only hydrogen, carbon, nitrogen or oxygen atoms.

According to an embodiment, the thickness of the membrane ranges from 0.5 to 500 µm, more preferably from 2.5 to 100 µm, even more preferably from 5 to 50 µm.

Membrane thickness can be easily determined by any method known of the person skilled in the art. An example of method for measuring membrane thickness is the following: thickness is measured in situ with an optical spectrometer (for example V8E—Specim) assembled on an optical microscope (for example Olympus). The focus is set strictly at the interface where the membrane grows. Another example of method for measuring membrane thickness is the following: thickness is measured ex situ with an optical profilometer (for example Microsurf 3D—Fogale nanotech) by transferring the membrane from the liquid to a glass slide.

According to an embodiment, the interfacial shear storage modulus G' of the polymer membrane, measured at 1 rad/s, is at least 0.1 N/m, preferably 0.5 N/m, more preferably at least 1.0 N/m, even more preferably at least 5.0 N/m (Pa·m). In one embodiment, the shear storage modulus G' of the membrane is about 10 N/m.

Interfacial shear storage modulus can be easily determined by any method known of the person skilled in the art. An example of method for measuring interfacial shear storage modulus is the following: a rheometer (for example AR-G2—TA Instruments) is used with a Double-Wall-Ring geometry. Torque measurement resolution is 1 nN/m. The ring-shaped container is half-filled with approximatively 21 mL of water solution until obtaining a flat interface pinned horizontally between the walls' edges, so the meniscus deformation can be neglected. Then, the ring is carefully approached to the interface and precisely placed to keep a flat interface between the wall corner and the diamond-shaped corner of the ring. Finally, the rest of the container is slowly filled with the same volume of oil. Measurements are controlled by TRIOS software (TA Instruments). The ring is oscillated and a strain rate of 0.1% is imposed to ensure that the measurements are all carried out in the linear regime.

In one embodiment, the interfacial shear storage modulus G' of the polymer membrane at an interphase between an oil phase and an aqueous phase having a pH about 3, measured at 1 rad/s, is at least 0.1 N/m, preferably 0.5 N/m, more preferably at least 1.0 N/m, even more preferably at least 5.0 N/m (Pa·m). In one embodiment, the shear storage modulus G' of the membrane is about 10 N/m.

According to an embodiment, the hydrogen bond donor polymer and the hydrogen bond acceptor polymer are bounded together by means of hydrogen bounds. According to another embodiment, the hydrogen bond donor polymer and the hydrogen bond acceptor polymer are bounded together by means of hydrophobic interactions. In one embodiment, the hydrogen bond donor polymer and the hydrogen bond acceptor polymer are bounded together by means of hydrogen bounds and hydrophobic interactions.

According to an embodiment, the membrane is not a complex wherein hydrogen bond donor polymer and the hydrogen bond acceptor polymer are oppositely charged polymers.

According to an embodiment, the membrane is substantially free of polymerization residues such as monomers, or does not comprise any polymerization residues.

According to an embodiment, the membrane is substantially free of amodimethicone, PAA carbomer, alginate and/or calcium ions, or does not comprise any amodimethicone, PAA carbomer, alginate and/or calcium ions.

According to an embodiment, at a pH lower than 5, the hydrogen bond acceptor polymer is not a charged polymer, i.e. comprises less than 5% of charged monomers, in number of charged monomers relative to the total number of monomer units in the polymer. In one embodiment, at pH 4, the hydrogen bond donor polymer comprises less than 1%, preferably less than 0.5%, more preferably less than 0.25% of charged monomers, in number of charged monomers relative to the total number of monomer units in the polymer. In one embodiment, at pH 3, the hydrogen bond donor polymer is substantially free of charged monomers.

According to an embodiment, the hydrogen bond donor polymer is not a charged polymer. According to an embodiment, the hydrogen bond acceptor polymer is not a charged polymer. In one embodiment, the hydrogen bond donor polymer and the hydrogen bond acceptor polymer are not charged polymers.

According to an embodiment, the membrane is substantially free of charged polymers such as polycations. In one embodiment, the membrane does not comprise any charged polymers.

According to an embodiment, the membrane is stable at a pH lower than 3, preferably lower than 4. According to an embodiment, the membrane dissolves at a pH higher than 5, preferably higher than 5.5.

According to an embodiment, the membrane is self-repairing. In the context of the invention, "self-repairing" means that, during a manufacturing method wherein the membrane is placed in presence of both hydrogen bond donor and hydrogen bond acceptor polymer, if the membrane is locally damaged, then it assembles itself back in less than 3 hours, preferably in less than 2 hours, preferably about 1 hour, so that the break or the hole disappears.

The invention also relates to a method of manufacturing a polymer membrane comprising a hydrogen bond donor polymer and a hydrogen bond acceptor polymer.

The method according to the invention comprises a step of contacting an aqueous phase comprising a first polymer, and an oil phase comprising a second different polymer; wherein one polymer is a hydrogen bond donor polymer and the other polymer is a hydrogen bond acceptor polymer. Preferably, the amount of aqueous phase is greater than the amount of oil phase.

According an embodiment, the hydrogen bond donor polymer and/or the hydrogen bond acceptor polymer used in the method are selected from any hydrogen bond donor polymer and/or any hydrogen bond acceptor polymer as previously described.

According to an embodiment, the two polymers assemble spontaneously by means of hydrogen bounds. According to another embodiment, the two polymers assemble spontaneously by means of hydrophobic interactions. In one embodiment, the two polymers assemble spontaneously by means of hydrogen bounds and/or hydrophobic interactions.

According to an embodiment, the method is proceeded at a pH lower than 7, preferably lower than 6, more preferably lower than 5, even more preferably lower than 4, even more preferably about 3.

According to an embodiment, at least one among first and second polymers is not a charged polymer. In one embodiment, both first and second polymers are not charged polymers.

According to an embodiment, the oil phase comprises a polar oil. In one embodiment, the oil phase comprises a polar oil selected from fatty substances, vegetable oils, mineral oils, animal oils, and mixtures thereof. In one specific embodiment, the fatty substance is selected from esters of fatty alcohols and esters of fatty acids such as isopropyl myristate, glycerol myristate, isononyl palmitate, caprylic acid or capric acid triglycerides, isopropyl palmitate or ethyl palmitate, typically $C_1$-$C_{20}$, silicone oil, polysiloxane, and mixtures thereof. In one specific embodiment, the vegetable oil is selected from sweet almond oil, jojoba oil, palm oil, phytosqualane, and mixtures thereof. In one specific embodiment, the animal oil is squalene. In one more specific embodiment, the polar oil is selected from isopropyl myristate, medium chain triglycerides such as Miglyol® 812N (caprylic/capric medium chain triglycerides), olive oil (oleic acid/(9Z)-Octadec-9-enoic acid), and mixtures thereof. Typically, the polymer which is present in the oil phase is soluble in said oil phase. By "soluble", it is meant that after introduction of the polymer into the oil phase, the oil phase is transparent when observed at the naked eye.

According to an embodiment, the aqueous phase comprises water. According to an embodiment, the aqueous phase consists in water, ions obtained from dissociation of acids and bases for pH adjustment such as hydrochloric acid (HCl) and sodium hydroxide (NaOH) and a polymer precursor of the membrane.

According to an embodiment, the method does not use amodimethicone, PAA carbomer, alginate and/or calcium ions.

According to an embodiment, the thickness h (unit: m) of the membrane obtained from the method is related to the contact time t (unit: s) and the coefficient of diffusion D (unit: m²/s) and a constant $H_0$ (unit: m) according to the formula:

$$h = H_0 + (D^* t)^{1/2}.$$

In one embodiment, $H_0$ is about $10^{-7}$ m. In one embodiment, D is about $10^{-17}$ m²/s.

In one embodiment, the thickness of the membrane obtained from the method after 2 h ranges from 0.1 to 25 µm, more preferably from 0.2 to 5 µm, even more preferably from 0.1 to 1 µm, even more preferably about 0.4 µm.

In one embodiment, the thickness of the membrane obtained from the method after 100 days ranges from 0.5 to 500 µm, more preferably from 2.5 to 100 µm, even more preferably from 5 to 50 µm, even more preferably about 10 µm.

According to an embodiment, the interfacial shear storage modulus G' of shell obtained from the method after 2 hours, measured at 1 rad/s, is at least 0.1 N/m, preferably 0.5 N/m, more preferably at least 1.0 N/m, even more preferably at least 5.0 N/m (Pa·m). In one embodiment, the shear storage modulus G' of the membrane is about 10 N/m.

This invention also relates to a capsule comprising a core and a shell around said core, wherein said shell comprises a polymer membrane as previously described.

According to an embodiment, the core comprises a substance of interest. In one embodiment, the substance of interest is pure or included in a solvent such as an oil or an aqueous solution. According to an embodiment, the substance of interest is a biologically active substance, for example a cosmetically or therapeutically active substance. According to an embodiment, the substance of interest is a cosmetically or therapeutically active substance.

According to an embodiment, the core comprises an oil. In one embodiment, the core comprises a polar oil. In one specific embodiment, the core comprises a polar oil selected from fatty substances, vegetable oils, mineral oils, animal oils, and mixtures thereof as previously described.

According to an embodiment, the core comprises water.

According to an embodiment, the mean diameter of the capsules and/or of the shell ranges from 0.1 cm to 10 cm, preferably from 0.2 to 5 cm. According to another embodiment, the mean diameter of the capsules and/or of the shell ranges from 5 µm to 500 µm, preferably from 10 µm to 100 µm, more preferably from 20 to 50 µm. According to another embodiment, the mean diameter of the capsules and/or of the shell ranges from 0.05 µm to 20 µm, preferably from 0.1 µm to 10 µm, more preferably from 0.25 µm to 5 µm.

According to an embodiment, the thickness of the membrane of the capsule ranges from 50 nm to 50 µm.

According to an embodiment, the interfacial shear storage modulus G' of the shell, measured at 1 rad/s, is at least 0.1 N/m, preferably 0.5 N/m, more preferably at least 1.0 N/m, even more preferably at least 5.0 N/m (Pa·m).

According to an embodiment, the shell is stable at a pH lower than 3, preferably lower than 4. According to an embodiment, the shell dissolves at a pH higher than 5, preferably higher than 5.5. This property might be advantageous when the core is intended to be released when the capsule is placed in appropriate pH conditions.

The invention also relates to a composition comprising a polymer membrane as previously described and/or comprising capsules as previously described.

The invention also relates to a composition comprising a dispersion of oil droplets in an aqueous phase, wherein each oil droplet is coated by a polymer membrane as previously described, wherein
either the hydrogen bond donor polymer is present in the aqueous phase and the hydrogen bond acceptor polymer is present in the oil droplets,
or the hydrogen bond donor polymer is present in the oil droplets and the hydrogen bond acceptor polymer is present in the aqueous phase.

According an embodiment, the composition is a consumer product for example a composition for use in household applications, such as a liquid or powder detergent, a composition for personal care. According to an embodiment, the composition is a cosmetic composition such as soap, a shampoo or a body cream. According to an embodiment, the composition is a pharmaceutical composition such as a solution for use by oral, topical or systemic administration.

Preferably, the polymer membrane of the invention, and/or the method of manufacture of the invention, and/or the composition of the invention, and/or the capsule according to the invention, are substantially free of any surfactant. By "substantially free of any surfactant", it is meant that the polymer membrane of the invention, and/or the method of manufacture of the invention, and/or the composition of the invention, and/or the capsule according to the invention, comprise or use less than 2% by weight of surfactant, preferably less than 1% by weight of surfactant, preferably less than 0.5% by weight of surfactant, and more preferably are devoid of any surfactant.

The invention also relates to a method of encapsulation comprising a step of manufacturing a polymer membrane as previously described and/or a capsule as previously described.

The invention also relates to a method of encapsulation comprising the method of manufacturing a polymer membrane as previously described.

According to a first embodiment, the method of encapsulation comprises a step of dripping an oil phase comprising a first polymer into an aqueous phase comprising a second different polymer; or a step of dripping an aqueous phase comprising a first polymer into an oil phase comprising a second different polymer; wherein one polymer is a hydrogen bond donor polymer and the other polymer is a hydrogen bond acceptor polymer.

According to a second embodiment, the method of encapsulation comprises a step of shearing an oil phase comprising a first polymer with an aqueous phase comprising a second different polymer using a rotor-stator homogenizer; wherein one polymer is a hydrogen bond donor polymer and the other polymer is a hydrogen bond acceptor polymer.

According to a third embodiment, the method of encapsulation comprises a step of contacting by means of a flow-focusing unit an oil phase comprising a first polymer with an aqueous phase comprising a second different polymer using a microfluidic chip; wherein one polymer is a hydrogen bond donor polymer and the other polymer is a hydrogen bond acceptor polymer.

EXAMPLES

Figure 1:
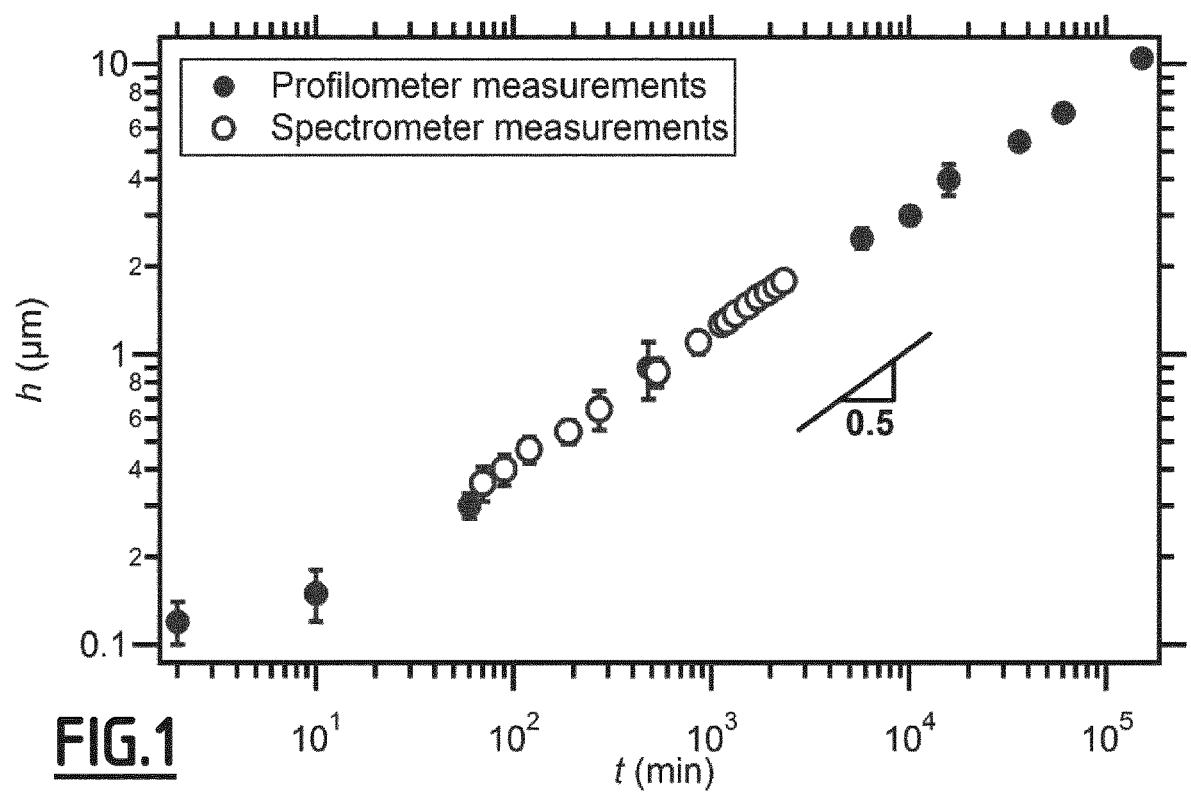
FIG. 1 is a graph showing the evolution of the thickness (h) of a polymeric membrane according to the invention over time (t) as discussed in Example 2, measured by two methods: in situ spectrometry (empty circles) and ex situ profilometry (filled circles). Error bars are shown when larger than markers size.

The present invention is further illustrated by the following examples.

Example 1: Polymers for Manufacturing a Polymeric Membrane

Hereafter are provided examples of hydrogen bond donor and hydrogen bond acceptor polymers susceptible to be combined to create a polymeric membrane according to the invention.

TABLE 1

| # | Hydrogen bond donor polymer | Hydrogen bond acceptor polymer |
|---|---|---|
| 1 | PMAA | PPO |
| 2 | PMAA | PVA-PVAc 25%-75% |
| 3 | PMAA | PPO-PEO (L61, L81, L101, L121, 17R4 or 31R4) |
| 4 | PEAA | PPO-PEO (L44, L64, P84, P104, P65, P75, P85 or P105) |
| 5 | PSMA | PPO |
| 6 | PSMA | PVA-PVAc 25%-75% |
| 7 | PSMA | PPO-PEO (L61, L81, L101, L121, 17R4 or 31R4) |
| 8 | PVA-PVAc 75%-25% | PPO |
| 9 | PVA-PVAc 75%-25% | PVA-PVAc 25%-75% |
| 10 | PVA-PVAc 75%-25% | PPO-PEO (L61, L81, L101, L121, 17R4 or 31R4) |
| 11 | PMAA | PDMAEMA |

Hereafter are provided the hydrogen bond donor and hydrogen bond acceptor polymers previously listed, classified according to their hydrophilic character (more water-soluble than oil-soluble) or their hydrophilic character (more oil-soluble than water-soluble).

TABLE 2

| Hydrophilic polymer | Type |
|---|---|
| poly(methacrylic) acid (PMAA) | H bond donor |
| styrene-maleic acid copolymer (PSMA) | H bond donor |
| Poly(vinyl) alcohol (PVA) - Poly(vinyl) acetate (PVAc) 75%-25% | H bond donor |
| polypropylene oxide (PPO)-polyethylene oxide (PEO) copolymer selected from: L44, L64, P84, P104, P65, P75, P85 and P105 | H bond acceptor |

TABLE 3

| Lipophilic polymer | Type |
|---|---|
| poly(ethylacrylic) acid (PEAA) | H bond donor |
| polypropylene oxide (PPO) | H bond acceptor |
| polypropylene oxide (PPO)-polyethylene oxide (PEO) copolymer selected from: L61, L81, L101, L121, 17R4 and 31R4 | H bond acceptor |
| Poly(vinyl) alcohol (PVA) - Poly(vinyl) acetate (PVAc) 25%-75% | H bond acceptor |
| poly(dimethylaminoethyl methacrylate) (PDMAEMA) | H bond acceptor |

Examples of embodiments of the manufacturing method of the invention consists in contacting at a water-oil interface one hydrophilic polymer from Table 2 solubilized in an aqueous medium and one lipophilic polymer from Table 3 solubilized in an oil medium, to obtain a polymer membrane according to the invention.

Example 2: Polymer Membrane and Manufacture Thereof

Hereafter is detailed the manufacture of a polymer membrane according to the invention comprising poly(methacrylic acid) (PMAA) as hydrogen bond donor polymer and poly(propylene oxide) (PPO) as hydrogen bond acceptor polymer.

Materials and Methods

Water-based solution is prepared by dissolution of 1 wt % of PMAA (molar mass: 100 000 g/mol) (Poly-sciences, Inc.) in water-distilled and purified with milli-Q apparatus (Millipore). Molar mass of a repeat unit MAA is 87:1 g/mol, which corresponds to a molar concentration of 0:11 mol/L. pH is adjusted at 3 by adding hydrochloric acid (HCl) (Sigma-Aldrich) solution concentrated at 1 M or sodium hydroxide solution (NaOH) (Sigma-Aldrich) solution at the same concentration and measured with pH-meter pHM 250 ion analyser Meterlab (Radiometer Copenhagen) with a precision of 0.05 pH.

Oil-based solution is prepared by dissolution of 1 wt % (weight by weight) of PPO (molar mass: 4000 g/mol) (Sigma-Aldrich) in isopropyl myristate (Sigma-Aldrich) or in Miglyol 812N (IMCD France/Sasol). Miglyol is a neutral oil consisting of caprylic/capric triglyceride ($C_8/C_{10}$ chains). Molar mass of a repeat unit PO is 58:1 g/mol, which corresponds to a molar concentration of 0:15 mol/L. We choose 1 wt % for both polymers to ensure an excess of polymer in bulk phases with respect to the interface, while being in dilute regime (<3 wt %) to have a low viscosity solution, hence a better sensitivity to interfacial rheology measurements.

To manufacture the polymer membrane, the aqueous phase is put into contact with the oil phase.

Membrane thickness is measured in situ with an optical spectrometer V8E (Specim) assembled on an optical microscope (Olympus). The focus is set strictly at the interface where the membrane grows. Thickness is also measured ex situ with an optical profilometer Microsurf 3D (Fogale nanotech) by transferring the membrane from the liquid to a glass slide.

To probe interfacial rheometry, an AR-G2 rheometer (TA Instruments) is used with a Double-Wall-Ring geometry. Torque measurement resolution is 1 nN/m. The ring-shaped container is half-filled with approximatively 21 mL of water solution until obtaining a flat interface pinned horizontally between the walls' edges, so the meniscus deformation can be neglected. Then, the ring is carefully approached to the interface and precisely placed to keep a flat interface between the wall corner and the diamond-shaped corner of the ring. Finally, the rest of the container is slowly filled with the same volume of oil. Measurements are controlled by TRIOS software (TA Instruments). A strain rate of 0.1% is imposed to ensure that the measurements are all carried out in the linear regime.

Results

The membrane assembly was probed in a model plane geometry. To prepare a flat polymer membrane, the aqueous phase containing the hydrogen bond-donor polymer (PMAA) was put into contact with the oil phase containing the hydrogen bond-acceptor polymer (PPO).

The thickness of the membrane was measured either in situ using an optical spectroscope, or ex situ using an optical profilometer to analyze the membrane deposited from the liquid onto a glass slide.

The membrane grows continuously with time without reaching any saturation over months and its thickness is 10 μm after 100 days as shown in FIG. 1. The thickness, which scales as $t^{1/2}$, suggests a diffusion-limited mechanism. The associated diffusion coefficient has been determined from the extrapolated intercept of the long-time regime in FIG. 1. The obtained value was of the order of $10^{17}$ m$^2$/s, which is much lower than the diffusion coefficient of the polymers in the bulk phases. This suggests that the growth of the membrane was controlled by the diffusion of the polymer molecules through the membrane to complex with their hydrogen-bond partner.

Figure 2:
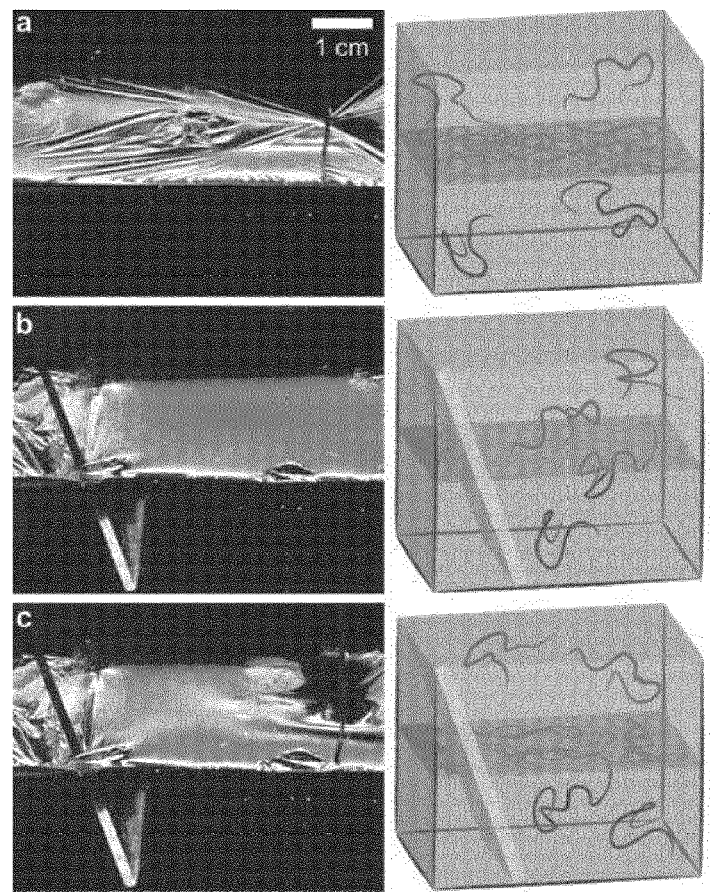
FIG. 2 is a combination of pictures and sketches illustrating the formation of wrinkles upon gentle pressure (3-$a$), the removal by a plate (3-$b$) and the subsequent restoration (3-$c$) of a polymeric membrane according to the invention, as disclosed in Example 2.

This model geometry further allows probing the self-healing properties of the flat membrane as shown in FIG. 2. The presence of the membrane at the oil-water interface was revealed by the formation of wrinkles as a gentle strain was applied with a spatula (FIG. 2-a). Using a microscope cover slide, the initial polymer membrane was pushed on the side, which allowed a fresh one to appear (FIG. 2-b). A few seconds later, wrinkles could be seen at the oil-water interface as the membrane was gently pressed with a spatula again (FIG. 2-c). This simple test showed that the membrane reassembled quickly from the oil and water reservoirs of polymer molecules.

Figure 3:
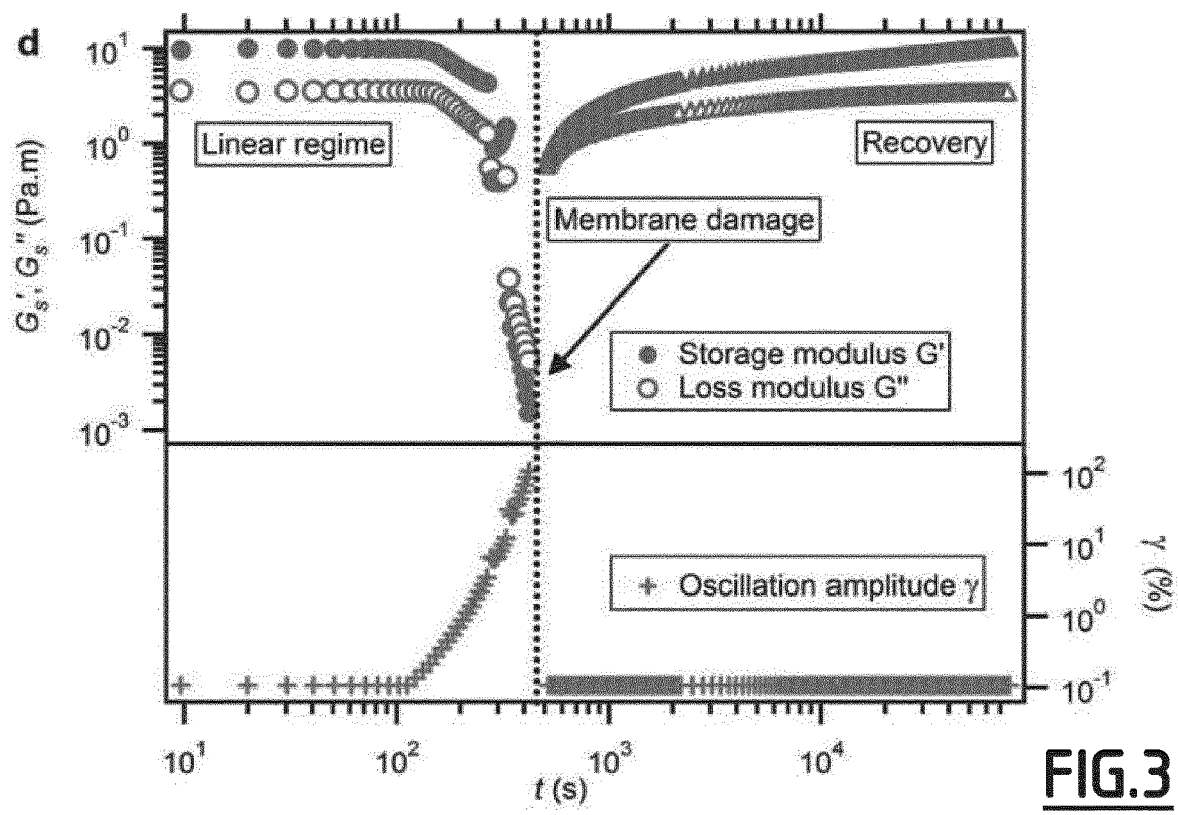
FIG. 3 is a graph showing the evolution of the interfacial storage modulus $G'_s$ (filled circles) and of the interfacial loss modulus $G''_s$ (empty circles) of a polymeric membrane according to the invention as a function of strain, which evidence that it can self-repair after being damaged, as disclosed in Example 2. Frequency is 1 rad·s$^{-1}$.

A double-wall-ring interfacial shear rheometer was used to measure the surface shear storage and loss moduli of the membrane, $G'_s$ and $G''_s$, respectively, with increasing deformation amplitudes from 0.1% to 100%. At deformation amplitude of 0.1%, the surface shear storage modulus was about 10 N/m (FIG. 3). Above a critical strain, which is about 0.5%, the system was no longer in the linear regime and both moduli drop by several orders of magnitude (FIG. 3). A visual inspection of the interface indicated that the membrane is damaged. However, when the deformation was decreased again, the initial values of the moduli were recovered in about an hour. These results suggested that the membrane easily rearranged through diffusion of the polymer molecules towards and inside the membrane, owing to the hydrogen bond non-covalent interactions.

These results evidence that a polymer membrane can be formed at the interface of a water-oil system by contacting a hydrogen bond-donor polymer included in an aqueous phase with a hydrogen bond-acceptor polymer included in the oil phase.

Comparative Example 2: Polymer Membrane According to WO2014/064255

A comparative polymer membrane of 5 layers of PMAA and PVP has been made according to example 1 of WO2014/064225.

The surface shear storage modulus G' of the obtained global layer has been measured as in example 2 above.

The value was about 0.2 N/m at 1 rad/s.

Example 3: Capsules and Manufacture Thereof

Hereafter is described the assembly around oil droplets of the polymer membrane of Example 2, for encapsulation purposes.

Material and Methods

Emulsions have been prepared in vials by gently pouring 6 mL of water-based solution and then 4 mL of oil-based solution as described in Example 2. An Ultra-Turrax disperser (IKA) was used to form an emulsion with a speed of 20000 rpm during 30 seconds.

The microfluidic device was first designed with a dedicated software (Clewin) and printed on a mask. Then a SU-8 negative photoresist resin (Micro Chem) was spin-coated with the desired thickness on a silicon wafer. Two-layer lithography were used with no intermediate step (Leman, M. et al., Lab on a Chip, Vol. 15, 2015, pp. 753-765). The obtained silica mold was filled with PDMS (poly(dimethylsiloxane)) (Sylgard 184, Dow Corning) mixed with 10% (w/w) curing agent and incubated at 70° C. for about 4 hours. The PDMS was peeled off the mold and the entrances and exits were punched with a 0.5 mm-diameter Harris Uni-Core biopsy punch (Electron Microscopy Sciences). The PDMS was finally sealed to a glass slide with a PDC-002 oxygen plasma cleaner (Harrick Plasma). Every entrance or exit of the chip was connected through PEEK (poly(etheretherketone)) tubings to a small vial. Applied pressures in vials (about 400 mbar) were controlled by a MFCS pump (Fluigent).

Results

Figure 4:
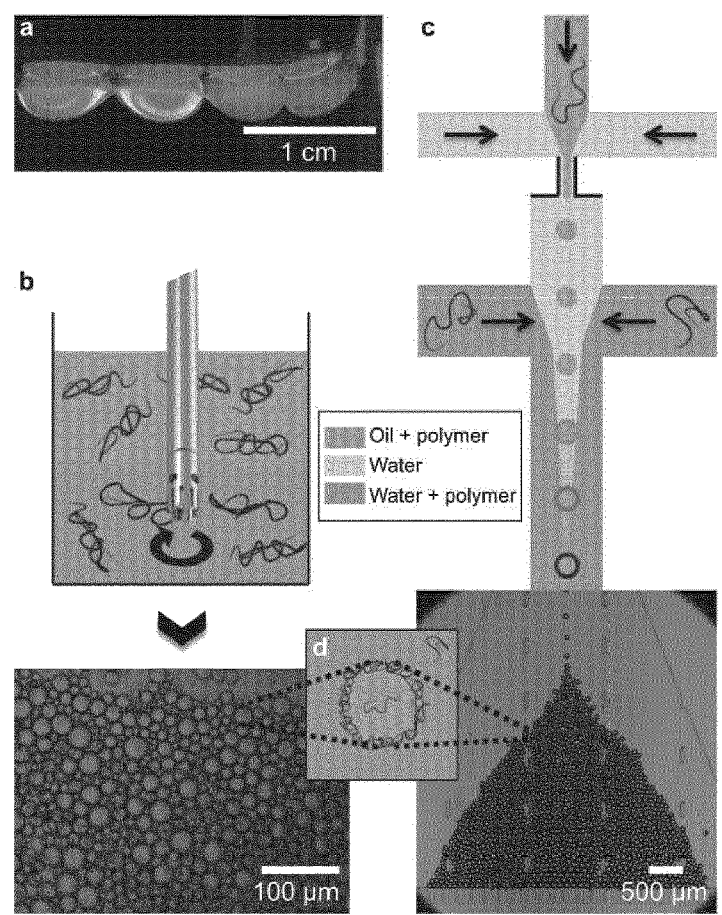
FIG. 4 is a combination of pictures and sketches showing centimeter-sized capsules formed by dripping of droplets (4-$a$), the formation of capsules with a diameter of 25 µm±10 µm using a rotor-stator homogenizer (4-$b$), and formation of monodisperse population of micron-sized capsules by using a microfluidic chip (4-$c$), as disclosed in Example 3.

First, centimeter-sized capsules have been produced by gently dripping oil drops containing PPO into a water phase containing PMAA (FIG. 4-a).

Secondly, using a rotor-stator homogenizer and by shearing the two fluid phases containing the polymers, capsules with a diameter of 25 µm±10 µm (FIG. 4-b) have been manufactured. This one-step process enables the preparation of microcapsules that are stable for months.

Thirdly, microfluidics was used to produce a monodisperse population of micron-sized capsules. The microfluidic chip was composed of a flow-focusing unit where oil droplets containing PPO were produced in a pure aqueous phase to avoid fast interfacial complexation at the constriction, which may plug the flow-focusing unit. The PMAA solution was then added right after to trigger the interfacial complexation at the oil-water interface. The capsules were finally collected in a chamber with a filter made by two-layer lithography, where they can be stored during several days (FIG. 4-c). This semi-permeable filter being permeable to the external aqueous phase but not to capsules, allows to increase the capsule concentration.

Even in close contact to each other, all capsules presented a unique stability compared to standard surfactant-stabilized emulsions and no coalescence was observed. It is especially the case for the centimeter-sized droplets which are known to be very difficult to stabilize, as the coalescence probability increases with the droplet size. Without being linked to any theory, the Applicant believes that the high interfacial rigidity of the polymer membranes protects the assembly against coalescence.

Interestingly, when increasing the pH from 3 to 6, it was observed that the shell of the capsule progressively dissolves, so that at a pH value of 5.5, the oil core of the capsule is released from the capsule. This property will advantageous when designing capsules wherein the core is intended to be released in acidic conditions.

The invention claimed is:

1. A polymer membrane comprising a hydrogen bond donor polymer and a hydrogen bond acceptor polymer;
   wherein said hydrogen bond donor polymer is made of one or more monomers, and comprises:
      a hydrogen bond donor group comprising carboxyl in at least 75% of the monomer units relative to the total number of monomer units in the polymer; and
      a lateral substituent comprising at least one hydrophobic group selected from the group consisting of alkyl, cycloalkyl and aryl, in at least 75% of the monomer units relative to the total number of monomer units in the polymer;
   wherein said hydrogen bond acceptor polymer is made of one or more monomers, and comprises:
      a hydrogen bond acceptor group comprising ether or ester in at least 75% of the monomer units relative to the total number of monomer units in the polymer; and
      a lateral substituent comprising at least one hydrophobic group selected from the group consisting of alkyl, cycloalkyl and aryl in at least 75% of the monomer units relative to the total number of monomer units in the polymer;
      wherein said hydrogen bond acceptor polymer is selected from the group consisting of polypropylene oxide (PPO), poloxamers and polyvinyl acetate (PVAc)-polyvinyl alcohol (PVA) copolymers;
   wherein said polymer membrane does not comprise any charged polymer,
   wherein the hydrogen bond donor polymer and the hydrogen bond acceptor polymer are linked together by hydrogen bounds; and
   wherein the shear storage modulus G' of said polymer membrane, measured at 1 rad/s, is at least 0.5 N/m.

2. The polymer membrane according to claim 1, wherein said hydrogen bond donor polymer is poly(methacrylic) acid.

3. The polymer membrane according to claim 1, wherein said hydrogen bond acceptor polymer is selected from the group consisting of polypropylene oxide and a poloxamers, wherein the poloxamer comprises an amount of polypropylene oxide monomer ranging from 50% to 100% in number of monomers relative to the total number of monomer units in the poloxamer.

4. A method of manufacturing a polymer membrane comprising contacting:
   an aqueous phase comprising a first polymer; and
   an oil phase comprising a second different polymer;
   wherein one of said first and second polymers is a hydrogen bond donor polymer and the other is a hydrogen bond acceptor polymer;
   wherein said hydrogen bond donor polymer and said hydrogen bond acceptor promoter are defined according to claim 1;
   and
   wherein both said first and second polymers are not charged polymers.

5. The method according to claim 4, wherein said hydrogen bond donor polymer is poly(methacrylic) acid.

6. The method according to claim 4, wherein said hydrogen bond acceptor polymer is selected from the group consisting of polypropylene oxide and poloxamers, wherein the poloxamer comprises an amount of polypropylene oxide monomer ranging from 50% to 100% in number of monomers relative to the total number of monomer units in the poloxamer.

7. The method according to claim 4, wherein both said first and second polymers assemble spontaneously by means of hydrogen bounds.

8. The method according to claim 4, wherein the shear storage modulus of the polymer membrane manufactured by said method, measured at 1 rad/s, is at least 0.5 N/m.

9. A capsule comprising a core and a shell around said core, wherein said shell comprises a polymer membrane according to claim 1.

10. A composition comprising a polymer membrane according to claim 1.

11. A composition comprising a dispersion of oil droplets in an aqueous phase, wherein each oil droplet is coated by a polymer membrane according to claim 1, wherein
either the hydrogen bond donor polymer is present in the aqueous phase and the hydrogen bond acceptor polymer is present in the oil droplets,
or the hydrogen bond donor polymer is present in the oil droplets and the hydrogen bond acceptor polymer is present in the aqueous phase.

12. A method of encapsulation comprising:
forming around a core a polymer membrane according to claim 1.

13. A method of encapsulation comprising the method of manufacturing a polymer membrane according to claim 4.

14. A composition comprising capsules according to claim 9.

15. A method of encapsulation comprising:
forming around a core a polymer membrane to manufacture a capsule according to claim 9.

16. The polymer membrane according to claim 1, wherein the shear storage modulus G' of said polymer membrane, measured at 1 rad/s, is at least 1.0 N/m.

17. The polymer membrane according to claim 1, wherein the shear storage modulus G' of said polymer membrane, measured at 1 rad/s, is at least 5.0 N/m.

18. The method according to claim 8, wherein the shear storage modulus of the polymer membrane manufactured by said method, measured at 1 rad/s, is at least 1.0 N/m.

19. The method according to claim 8, wherein the shear storage modulus of the polymer membrane manufactured by said method, measured at 1 rad/s, is at least 5.0 N/m.

* * * * *